United States Patent [19]

May

[11] Patent Number: 5,233,104
[45] Date of Patent: Aug. 3, 1993

[54] PROCESS FOR TRIFLUOROMETHYLATION OF AROMATIC COMPOUNDS

[75] Inventor: Donald D. May, Chadds Ford, Pa.

[73] Assignee: E. I. Du Pont de Nemours and Company, Wilmington, Del.

[21] Appl. No.: 937,231

[22] Filed: Aug. 27, 1992

[51] Int. Cl.$^5$ ............................................. C07C 22/00
[52] U.S. Cl. ....................................... 570/144; 570/145
[58] Field of Search .................................. 570/144, 145

[56] References Cited

U.S. PATENT DOCUMENTS

| | | | |
|---|---|---|---|
| 4,582,921 | 4/1986 | Burton et al. | 556/128 |
| 4,650,887 | 3/1987 | Burton et al. | 556/112 |
| 4,749,802 | 6/1988 | Burton et al. | 556/112 |
| 4,895,991 | 1/1990 | Burton | 570/144 |

FOREIGN PATENT DOCUMENTS

| | | |
|---|---|---|
| 137424 | 9/1983 | European Pat. Off. . |
| 1538366 | 3/1968 | France . |
| 50-011891 | 5/1975 | Japan . |
| 6010121 | 3/1981 | Japan . |
| 7142923 | 9/1982 | Japan . |
| 1156912 | 8/1969 | United Kingdom . |

*Primary Examiner*—Alan Siegel

[57] ABSTRACT

Aromatic compound are trifluoromethylated by reaction in the vapor phase with a dihalodifluoromethane in the presence of a copper/copper fluoride catalyst.

5 Claims, No Drawings

PROCESS FOR TRIFLUOROMETHYLATION OF AROMATIC COMPOUNDS

FIELD OF THE INVENTION

The invention relates to a process of preparing trifluoromethylated organic compounds.

BACKGROUND AND PRIOR ART

Trifluoromethylated aromatic compounds have a number of important utilities. They find use as herbicides, pesticides and fungicides. Certain of these compounds are pharmaceutically active. There is a continuing need to produce trifluoromethylated aromatic compounds in an efficient and inexpensive manner, using readily available starting materials.

Trifluoromethylation is known in the art and has been practiced commercially by, for example, treating trichloromethyl benzene with hydrogen fluoride over a metal catalyst. It is desirable to avoid use of hydrogen fluoride, which is corrosive and extremely dangerous.

It is also known to carry out trifluoromethylation using fluorinating agents which already contain the trifluoromethyl group, such as trifluoromethyl iodide or bis(trifluoromethyl)mercury. Such processes involve use of expensive starting materials, and the processes themselves are difficult and produce significant amounts of undesired byproducts.

U.S. Pat. No. 4,895,991 teaches the preparation of trifluoromethyl organometallic reagents from dihalodifluoromethanes. A copper reagent is prepared by reacting the zinc or cadmium organometallic compound with cuprous bromide. Preparation of trifluoromethyl aromatics in solution is disclosed using DMF, metallic copper or copper-bronze, aromatic iodide, and $CF_2BrX$, where $X = Br$ or $Cl$.

SUMMARY OF THE INVENTION

A process is disclosed for preparing trifluoromethylated organic compounds in a vapor phase reaction using inexpensive, readily available precursors. The process comprises a single step reaction, wherein vapors of the aromatic reactant are contacted with dichlorodifluoromethane vapor in the presence of a catalyst comprising a mixture of copper and copper fluoride at a temperature of 300°–375° C.

In preferred aspects, the reaction is carried out using substantially equimolar amounts of the aromatic compound and dichlorodifluoromethane. The preferred temperature is 325° C.

DESCRIPTION OF THE PREFERRED EMBODIMENTS

In the broadest aspect of the invention, the aromatic compound to be trifluoromethylated has the formula Ar—X wherein Ar is a C6 aromatic ring, preferably benzyl, and X is H or a substituent selected from halogen (F, Cl, Br, I), alkyl, or cyano. Optionally the aromatic compound may be further substituted. Preferred reactants are benzene and chlorobenzene. The choice of reactant will, of course, depend on the product desired.

The second reactant is a difluorodihalomethane of the formula $CF_2Y_2$, where $Y = Cl$ or Br. Both difluorodibromomethane and difluorodichloromethane (Freon  12) are readily available materials.

The process is carried out by contacting, in vapor phase, the aromatic compound and the difluorodihalomethane in the presence of catalyst. The reaction may be carried out in, for example, a heated reaction tube, the reaction tube containing a bed of the catalyst and having entry means allowing co-introduction of the aromatic and difluorodihalomethane vapors. Preferably the reactants are flowed into the reaction bed by a flow of nitrogen. The trifluoromethylated product is obtained by condensing and fractionating the effluent vapors from the reactor tube. One type of suitable apparatus for carrying out the reaction is described more fully in the examples which follow, and other suitable reaction apparatus would be apparent to those skilled in the art.

The catalyst comprises a mixture of copper metal and copper fluoride. The ratio of metallic copper to copper fluoride is not currently considered to be critical. Ratios of $Cu:CuF_2$ of 10:1 to 100:1, in parts by weight, are satisfactory. It is critical, however, that the catalyst contain at least some copper fluoride, for the presence of copper fluoride has been found to overcome the problem of telomer formation which can arise when difluorodichloromethane is heated in the presence of a metallic copper surface.

The reaction is carried out at a temperature of 300°–375° C. Below 300° C, virtually no reaction occurs. The upper limit is effectively set by the temperature at which copper chloride, a byproduct of the reaction, begins to undergo fusion. A temperature of 325° C. is currently most preferred, and has resulted in very good product selectively and yield.

Different position isomers of the product are generated during the reaction. For example, if the starting aromatic is chlorobenzene, the reaction will produce the ortho, meta and para position isomers of trifluoromethylchlorobenzene, the relative amounts of which will depend on a number of factors, including the types of reactants and the reaction conditions. It has been found that the reaction which occurs is hydrogen substitution reaction, rather than a halogen substitution reaction such as occurs in many solvent-based trifluoromethylation reactions. This is advantageous over the prior art, in that the halogen is not replaced on the aromatic ring.

The relative amounts of aromatic reactant and difluorodihalomethane reactant are not currently believed to be critical to the reaction. Satisfactory results have been obtained using substantially equimolar amounts of the two reactants.

The Examples which follow will illustrate certain preferred embodiments of the invention, and are provided as illustration and not as limitation.

EXAMPLE 1

The reaction apparatus employed is comprised of a 0.5 inch by 12 inch stainless steel tube wrapped with external heating tape, and having attached heated feed lines for nitrogen purge gas, dichlorodifluoromethane and aromatic compound which is fed by a mechanical pump. The tube is charged with 27 g of 40 mesh copper metal and 0.50 g copper fluoride, which are premixed intimately. The reactor tube is heated to 375° C. using the heating tape. Once the tube has reached 375° C., $CF_2Cl_2$ is fed into the system at 5 ml/min. After several minutes feed, chlorobenzene is fed at 0.02 ml/min, by a positive displacement pump, into a preheated zone at 300° C., and then into the tube containing copper/copper fluoride catalyst. A sample of the effluent gas is analyzed by GC-MS (gas chromatography-mass spectroscopy) and contains ortho, meta, and para isomers of chlorotrifluoromethylbenzene in the ratio of 44%, 22%, and 22% respectively. The total amount of chlorobenzene converted to chlorotrifluoromethylbenzene is 40%. The gas is collected by condensation and the product is recovered from the liquid stream by fractional distillation.

EXAMPLE 2

Example 1 is repeated, except that benzene is fed instead of chlorobenzene, and at a temperature of 325° C. The yield of trifluoromethylbenzene is 50%, based on starting benzene.

EXAMPLE 3

Example 1 is repeated, except that bromobenzene is fed instead of chlorobenzene, and the temperature is 325° C. The combined yield of ortho-, meta- and para-trifluoromethyl bromobenzene is 40% based on starting bromobenzene.

EXAMPLE 4

A series of reactions were carried out, using benzene as aromatic reactant and the apparatus of Example 1, to optimize certain process variables. Nitrogen flow rate was found to effect the product yields. In the particular apparatus used, an $N_2$ flow of nitrogen flow to 50 ml/min, reduced the conversion to 20%. A decrease in the nitrogen flow to 20 ml/min also reduced the conversion, to 30%. The reflects that the optimum nitrogen flow for a given reactor can be determined empirically by those skilled in the art.

In the same reaction, increased benzene flow can also effect on the reaction. In the reaction shown in this Example, the benzene flow was set at a mole ratio to $CF_2Cl_2$ of 2.2 mmol/min. Increasing the benzene flow was found to decrease the trifluoromethylbenzene to benzene ratio in the product, and to increase the chlorobenzene levels present in the product.

The reaction of this Example, using benzene as aromatic reactant, was repeated at different temperatures. The effluent vapor was analyzed for unreacted benzene, chlorobenzene (by-product), and trifluoromethylbenzene. As indicated in Table 1, the subject reaction yielded the greatest amount of trifluoromethylbenzene at temperature of 325° C.

TABLE 1

| Temperature | % Benzene | % Chlorobenzene | % Trifluoromethylbenzene |
|---|---|---|---|
| 320 | 66.0 | 2.0 | 32.5 |
| 322 | 70.0 | 2.7 | 27.5 |
| 325 | 52.5 | 2.2 | 45.0 |
| 330 | 54.0 | 2.7 | 42.5 |
| 335 | 56.0 | 4.0 | 40.0 |
| 341 | 58.0 | 5.0 | 36.7 |

What is claimed is:

1. A process for trifluoromethylating an aromatic compound of the formula Ar—X, wherein Ar represents a C6 aromatic radical, and X represents halogen, hydrogen, alkyl, or a cyano group, comprising reacting the aromatic compound in the vapor phase with a difluorodihalomethane of the formula $CF_2Y_2$, wherein Y represents Cl or Br, at a temperature of 300°–375° C. in the presence of a catalyst comprising a mixture of copper metal and copper fluoride.

2. The process of claim 1 wherein Ar represents benzyl and X represents Cl.

3. The process of claim 1 wherein the temperature is about 325° C.

4. The process of claim 1 wherein the reactants are flowed through a heated bed of catalyst using a nitrogen flow.

5. The process of claim 1 further comprising separating the product from the effluent vapor by condensation and distillation.

* * * * *